(12) United States Patent
Miyata et al.

(10) Patent No.: US 9,259,557 B2
(45) Date of Patent: Feb. 16, 2016

(54) SHAFT AND GUIDEWIRE EMPLOYING THE SAME

(71) Applicant: ASAHI INTECC CO., LTD., Nagoya-shi, Aichi (JP)

(72) Inventors: Naohiko Miyata, Nagoya (JP); Muneya Furukawa, Seto (JP); Kenichi Matsuo, Izumiotsu (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 0 days.

(21) Appl. No.: 14/315,990

(22) Filed: Jun. 26, 2014

(65) Prior Publication Data

US 2015/0094691 A1    Apr. 2, 2015

(30) Foreign Application Priority Data

Oct. 2, 2013   (JP) .................................. 2013-207162

(51) Int. Cl.
*A61M 25/00* (2006.01)
*A61M 25/09* (2006.01)
*B21F 7/00* (2006.01)

(52) U.S. Cl.
CPC ......... *A61M 25/09016* (2013.01); *A61M 25/09* (2013.01); *A61M 2025/09075* (2013.01); *A61M 2025/09083* (2013.01); *A61M 2025/09108* (2013.01); *A61M 2025/09133* (2013.01); *A61M 2025/09191* (2013.01); *B21F 7/00* (2013.01)

(58) Field of Classification Search
CPC ............ A61M 25/09; A61M 2025/09; A61M 2025/09116; A61M 2025/09191; A61M 25/09016

USPC .......................................................... 600/585
See application file for complete search history.

(56) References Cited

U.S. PATENT DOCUMENTS

| | | | |
|---|---|---|---|
| 5,299,580 | A | 4/1994 | Atkinson et al. |
| 5,313,967 | A | 5/1994 | Lieber et al. |
| 6,059,771 | A | 5/2000 | Balbierz et al. |
| 8,113,916 | B2 | 2/2012 | Miller et al. |
| 2002/0043118 | A1 | 4/2002 | Claude |
| 2004/0142643 | A1 | 7/2004 | Miller et al. |
| 2004/0215109 | A1 | 10/2004 | Pingleton et al. |
| 2013/0304108 | A1 | 11/2013 | Weber et al. |
| 2014/0103273 | A1 | 4/2014 | Nakajima et al. |
| 2015/0094691 | A1 | 4/2015 | Miyata et al. |
| 2015/0094692 | A1 | 4/2015 | Miyata et al. |

FOREIGN PATENT DOCUMENTS

| | | |
|---|---|---|
| EP | 0 826 389 A2 | 3/1998 |
| EP | 2 163 276 A1 | 3/2010 |

(Continued)

OTHER PUBLICATIONS

Sep. 11, 2014 Search Report issued in European Patent Application No. 14173742.9.

(Continued)

*Primary Examiner* — Brian Szmal
(74) *Attorney, Agent, or Firm* — Oliff PLC

(57) ABSTRACT

A shaft suppresses a rise in operation resistance as it is pushed and pulled even inside an extremely winding blood vessel and thus secures sufficient torque transmission characteristics and operability. A guidewire may employ the above-described shaft. The shaft is twisted along its longitudinal axis and has a cross section that forms a substantially rectangular shape in a direction perpendicular to the longitudinal axis. Moreover, the cross section of the shaft has a projection that projects arcuately.

11 Claims, 8 Drawing Sheets

(56) References Cited

FOREIGN PATENT DOCUMENTS

| JP | 10216236 | 8/1998 |
| JP | 2008-155054 A | 7/2008 |
| JP | 2011-125556 A | 6/2011 |
| JP | A-2012-070906 | 4/2012 |
| JP | 2013-085781 A | 5/2013 |
| JP | 201570895 A | 4/2015 |
| JP | 201570896 A | 4/2015 |
| WO | WO 2012/172881 A1 | 12/2012 |

OTHER PUBLICATIONS

Mar. 12, 2015 Extended European Search Report issued in European Application No. 14173744.5.
Mar. 6, 2015 Extended European Search Report issued in European Patent Application No. 14173746.0.
U.S. Appl. No. 14/310,437, filed Jun. 20, 2014.
U.S. Appl. No. 14/316,229, filed Jun. 26, 2014.
Jul. 29, 2015 Office Action issued in U.S. Appl. No. 14/316,229.
Nov. 9, 2015 Office Action issued in Japanese Patent Application No. 2013-252887.
Nov. 17, 2015 Office Action issued in Japanese Patent Application No. 2013-207156.
Nov. 17, 2015 Written Directive issued in Japanese Patent Application No. 2013-207156.
Nov. 17, 2015 Office Action issued in Japanese Patent Application No. 2013-207162.
Nov. 17, 2015 Written Directive issued in Japanese Patent Application No. 2013-207162.

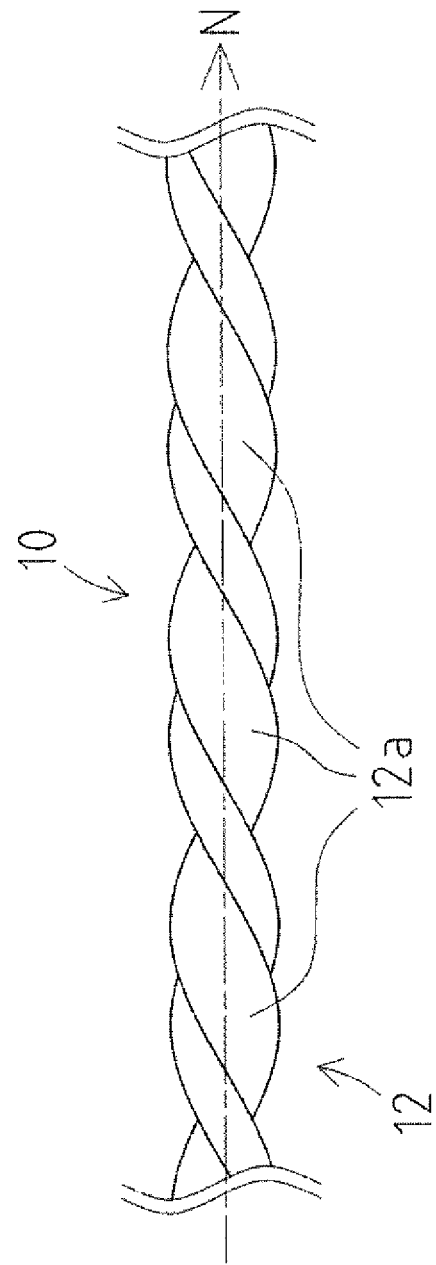

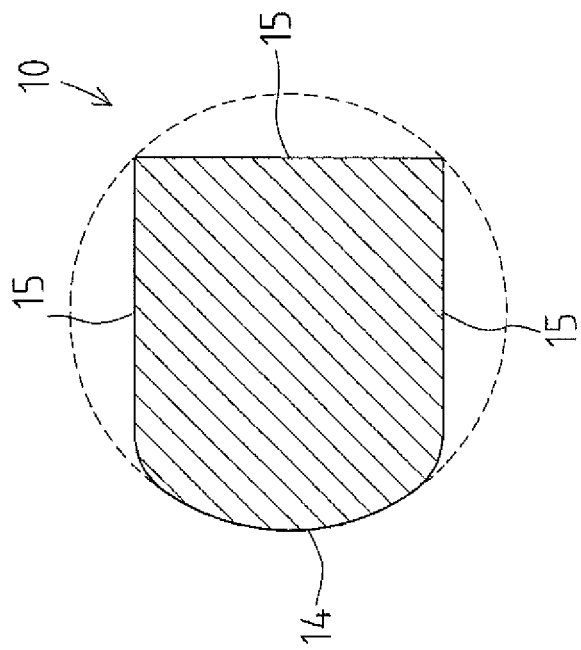
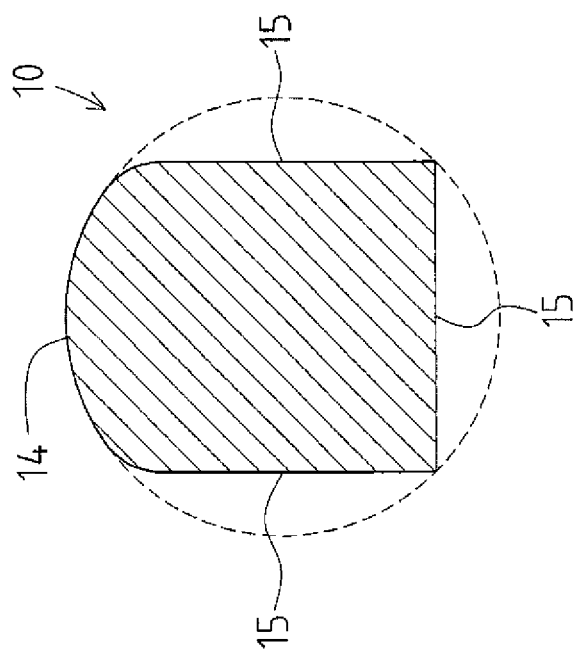

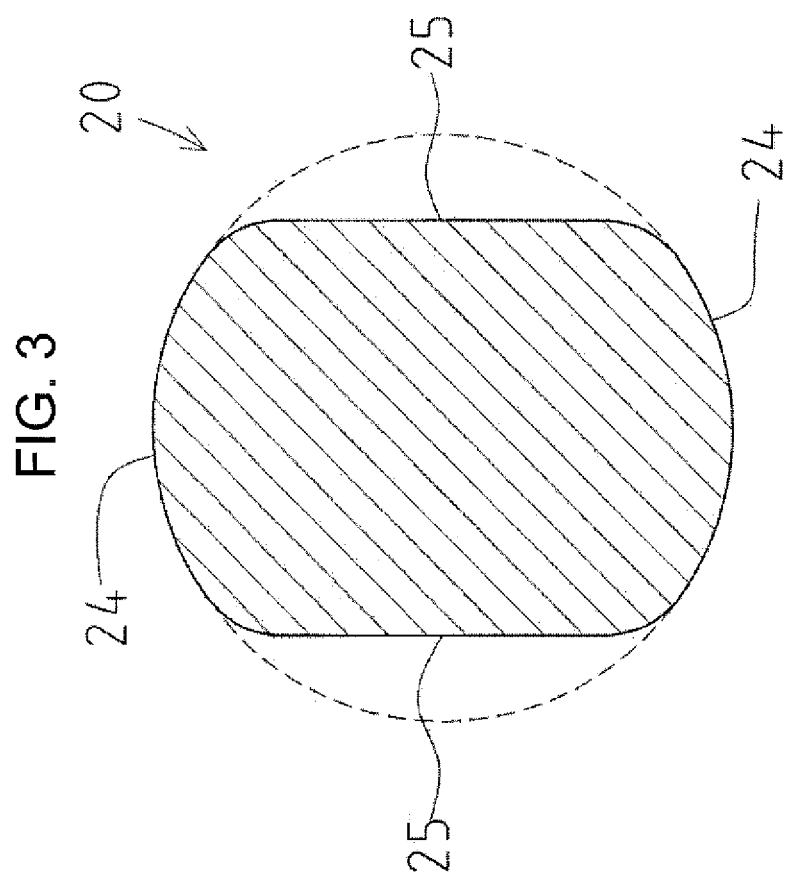

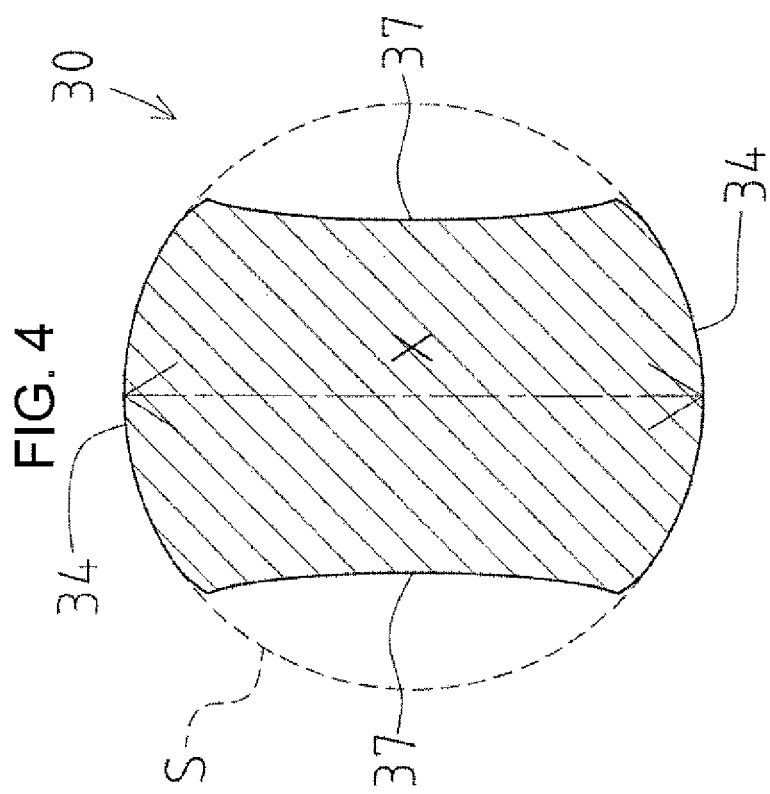

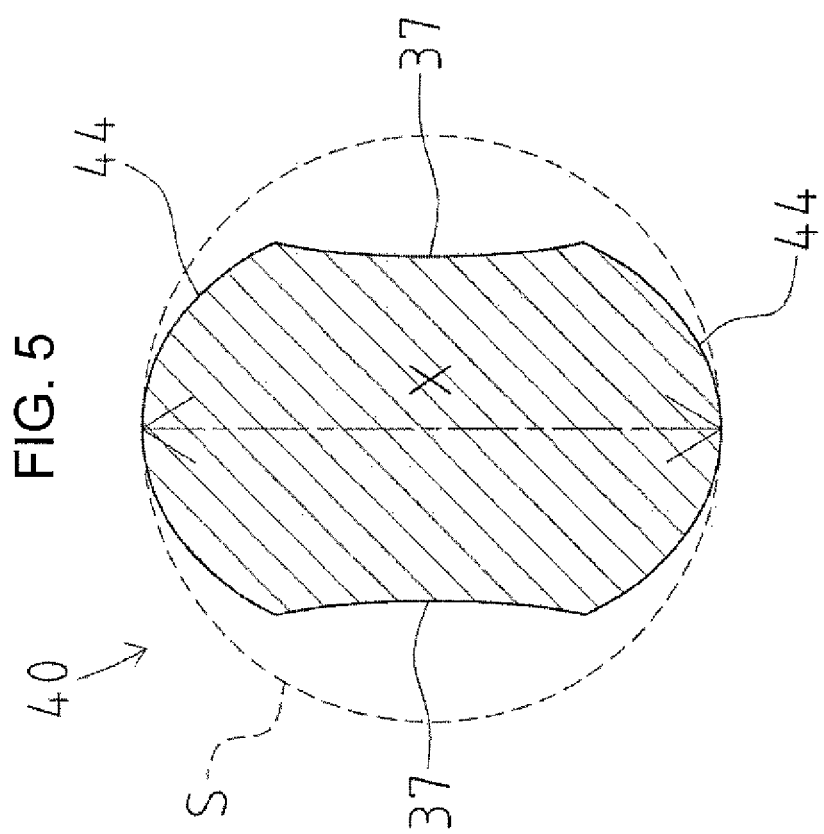

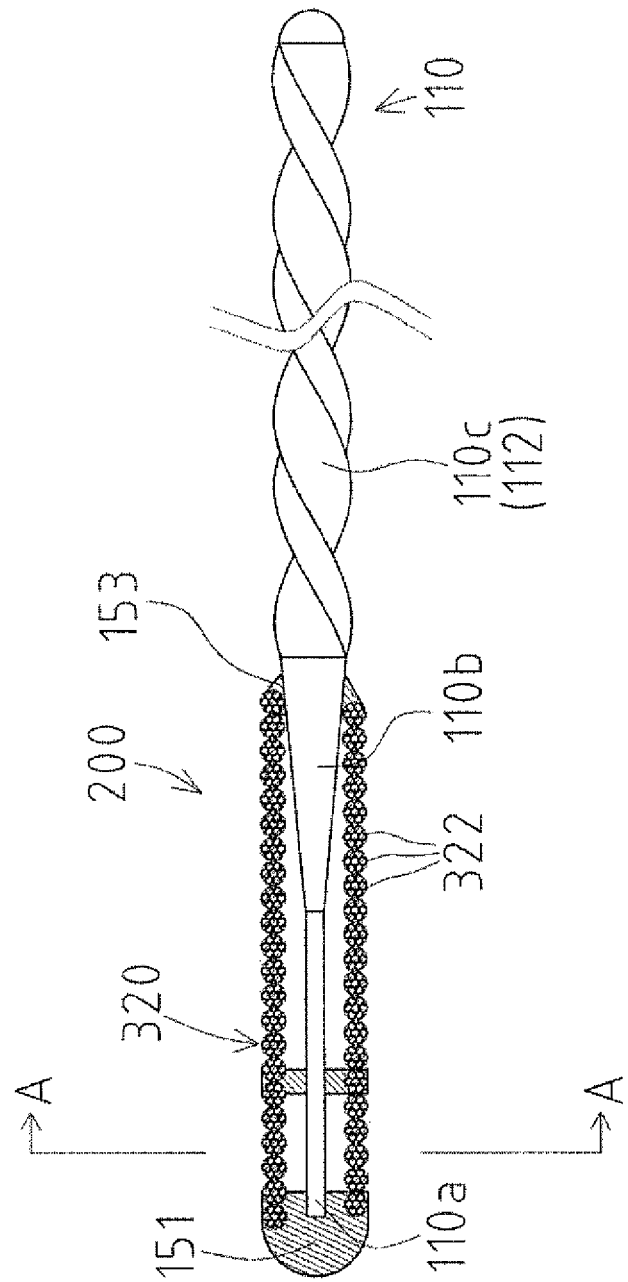

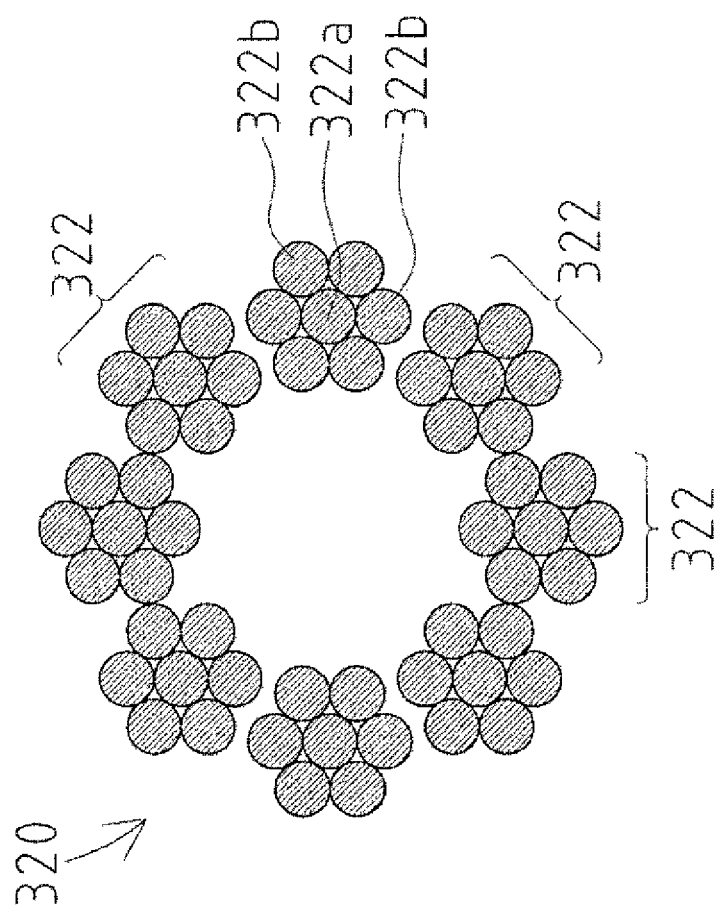

SHAFT AND GUIDEWIRE EMPLOYING THE SAME

CROSS-REFERENCE TO RELATED APPLICATION

This application claims priority to Japanese Application No. 2013-207162 which was filed on Oct. 2, 2013, the entire contents of which is incorporated herein by reference.

BACKGROUND

The disclosed embodiments relate to a medical device. Specifically, the disclosed embodiments relate to a shaft employed for a medical apparatus inserted into a body cavity for the purpose of treatment or an exam, and a guidewire employing the shaft.

Conventionally, various medical apparatuses inserted into a tubular organ and body tissue such as a blood vessel, a digestive tract and the ureter have been proposed for the purpose of treatment or examination.

For example, U.S. Patent Application Publication No. 2004/0215109 discloses a guidewire including a shaft twisted around a longitudinal axis.

SUMMARY

In the case of inserting a conventionally known guidewire along an inverted U-shaped path from the lower extremity vasculature of the right leg into the lower extremity vasculature of the left leg by, for example, the Cross-Over method, when passing through the top of such an extremely winding blood vessel, sliding against the blood vessel wall and the like cause an increase in operation resistance of a shaft as it is pushed and pulled. Accordingly, in a conventionally known guidewire, sufficient torque transmission characteristics are not obtained, possibly resulting in reduced operability.

The disclosed embodiments have been devised in view of such circumstances, and it is an object of the present invention to provide a shaft capable of suppressing the rise in operation resistance when the shaft is pushed and pulled, even inside an extremely winding blood vessel, to secure sufficient torque transmission characteristics so that operability is improved, and a guidewire employing the shaft.

In order to solve the above-described problem, a shaft and a guidewire employing the shaft according to one aspect of the present invention have the features below.

A shaft according to a first aspect of the present invention is a shaft that is twisted along its longitudinal axis, having a cross section that forms a substantially rectangular shape extending in a direction perpendicular to the longitudinal direction. The cross section further has at least one projection projected arcuately.

A second aspect of the present invention is the shaft according to the first aspect having a first projection and a second projection formed on a first pair of opposite sides of the cross section.

A third aspect of the present invention is the shaft according to the first aspect or the second aspect having a first recess and a second recess that are recessed arcuately on a second pair of opposite sides of the cross section.

A fourth aspect of the present invention is the shaft according to any one of the first to third aspects having a radius of curvature of the projection smaller than the radius of curvature of a virtual circle having a diameter equivalent to a length of the cross section in the first direction.

A fifth aspect of the present invention is a guidewire including a core shaft and a coiled body covering a distal portion of the core shaft. A proximal portion of the core shaft that is not covered by the coiled body is the shaft according to any one of the first to fourth aspects.

A sixth aspect of the present invention is the guidewire according to the fifth aspect having the coiled body composed of a plurality of helically wound strands, each strand being made of a plurality of twined wires.

The shaft of the first aspect is twisted along its longitudinal axis and has a cross section with a projection projecting arcuately. Thereby, when the shaft is inserted into a blood vessel, contact areas with a blood vessel wall are reduced due to many grooves generated by the twisting. At least one side among sides forming the cross section is projected arcuately, so that the top of the projected side comes into contact with the blood vessel wall.

Thus, as compared to a configuration without a projection projected arcuately (a configuration having a cross-sectional rectangular shape whose four corners are in contact with a blood vessel wall), the shaft reduces contact parts with a blood vessel wall, while having a smaller load applied to the blood vessel wall in contact with the shaft.

Therefore, when the above shaft rotates and enters the inside of a blood vessel, contact resistance against a blood vessel wall is reduced. Accordingly, operation resistance of the shaft as it is pushed and pulled is reduced so that torque transmission characteristics are enhanced, resulting in improved operability.

Moreover, even in a case where the above shaft is inserted along an inverted U-shaped path from the lower extremity vasculature of the right leg into the lower extremity vasculature of the left leg by, for example, the Cross-Over method, when passing through the top of a blood vessel, sliding against the blood vessel wall and the like does not suppress movement of the shaft, so that a distal portion of the shaft is allowed to be inserted deeply and smoothly into the blood vessel. In addition, it is possible to reduce damage of a blood vessel.

In the shaft of the second aspect, a first projection and a second projection are formed on a first pair of opposite sides of the cross section. Thereby, when inserting the shaft into a blood vessel, only top parts of the first and second projections formed on the first pair of sides come into contact with a blood vessel wall. Thus, as compared to a configuration without projections (a configuration having a cross-sectional rectangular shape whose four corners are in contact with a blood vessel wall), the above shaft reduces contact parts with a blood vessel wall, while also reducing a load applied to the blood vessel wall in contact with the shaft.

Therefore, when the above shaft rotates and enters the inside of a blood vessel, contact resistance against a blood vessel wall is reduced. Accordingly, the shaft brings beneficial results. That is, operation resistance of the shaft as it is pushed and pulled is further reduced so that sufficient torque transmission characteristics are secured, resulting in further enhanced operability.

The shaft of the third aspect has first and second recesses that are recessed arcuately on a second pair of opposite sides of the cross section. Thus, as compared to a configuration without sides recessed arcuately (a shaft having a cross-sectional rectangular shape), an area moment of inertial is lowered. Accordingly, for example, within a blood vessel of a lower extremity region extremely winding in an inverted U-shape, a permanent set (permanent deformation of the shaft) tends not to occur even in a case where the shaft bends excessively due to a load applied thereto when coming into contact with a blood vessel wall or the like. Thus, trouble in subsequent operation is prevented, thereby making it possible to use the shaft continuously.

In the shaft of the fourth aspect, the radius of curvature of a projection is smaller than the radius of curvature of a virtual circle whose diameter is equivalent to the length of the cross section of the shaft in the first direction. Such a shaft has a cross section in a tapered shape, and has the tops of two respective projections in contact with a blood vessel wall.

Therefore, as compared to a configuration without a projection (a configuration having a cross-sectional rectangular shape whose four corners are in contact with a blood vessel wall), contact areas (contact parts) with a blood vessel wall are reduced. Accordingly, when the above shaft rotates and enters the inside of a blood vessel, operation resistance of the shaft as it is pushed and pulled is reduced so that sufficient torque transmission characteristics are secured, resulting in further enhanced operability. Furthermore, it is possible to reduce damage of a blood vessel.

The guidewire of the fifth aspect includes a core shaft and a coiled body covering a distal portion of the core shaft, in which a proximal portion of the core shaft that is not covered by the coiled body is the shaft according to any one of the first to fourth aspects. Thereby, it is possible to obtain the above-described effects according to the first to fourth aspects. That is, it is possible to insert a distal portion of the guidewire even into an extremely winding blood vessel in an inverted U-shape deeply and smoothly, resulting in enhanced operability. Moreover, operation resistance of the guidewire as it is pushed and pulled is further reduced, while making it possible to reduce damage of a blood vessel effectively.

The guidewire of the sixth aspect includes a coiled body composed of a plurality of helically wound strands, each of the strands being made of a plurality of twined wires. Thus, as compared to a guidewire including a coiled body composed of, for example, a single wire having an external diameter nearly equal to that of the guidewire of the sixth aspect, flexibility of the coiled body is improved, and it is possible to secure sufficient torque transmission characteristics. Further, breaking strength against twisting is improved, so that safety of the guidewire is enhanced.

BRIEF DESCRIPTION OF DRAWINGS

FIG. 1 is a general view showing an embodiment of a shaft of the present invention.

FIGS. 2A and 2B are cross-sectional views showing a shaft of exemplary embodiments of the present invention.

FIG. 3 is a cross-sectional view showing a shaft of an exemplary embodiment of the present invention.

FIG. 4 is a cross-sectional view showing a shaft of an exemplary embodiment of the present invention.

FIG. 5 is a cross-sectional view showing a shaft of an exemplary embodiment of the present invention.

FIG. 7 is a general view showing an exemplary embodiment of a guidewire of the present invention.

FIG. 8 is a cross-sectional view along A-A of a coiled body in FIG. 7.

DETAILED DESCRIPTION OF EMBODIMENTS

Figure 6:
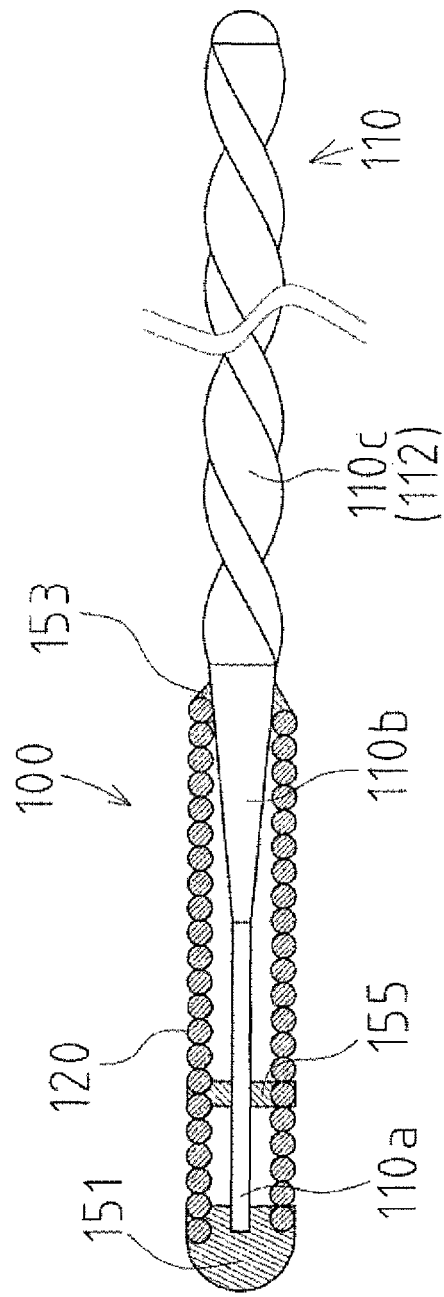
FIG. 6 is a general view showing an exemplary embodiment of a guidewire of the present invention.

Description will be given for a shaft based on embodiments shown in the drawings.

FIG. 1 is a general view showing an exemplary embodiment of a shaft of the present invention. Note that, in this figure, a length of the shaft is shortened to be schematically illustrated in whole in order to facilitate understanding. Thus, the dimensions shown are different from the actual dimensions.

As shown in FIG. 1, a shaft 10 is formed as a rod-like body in an elongated shape. The shaft 10 can be formed using materials such as but not limited to, for example, stainless steel (SUS304), a super elastic alloy such as a Ni—Ti alloy, and a piano wire.

The shaft 10 is twisted in a predetermined direction along a longitudinal axis N, and has a helically shaped portion 12. Additionally, the shaft 10 is provided with a plurality of grooves 12a at regular intervals along the longitudinal axis N. Thereby, for example, when inserting the shaft 10 into a blood vessel, the plurality of grooves 12a leads to a reduction of contact areas with a blood vessel wall.

Further, because the shaft 10 has the helically shaped portion 12, when a proximal side of the shaft 10 is rotated, such rotation is easily transmitted to a distal side of the shaft 10. That is, torque transmission characteristics are enhanced, resulting in improved operability.

Moreover, in FIG. 1, a direction of helix of the helically shaped portion 12 is counterclockwise along the longitudinal axis N of the shaft 10. However, the direction of helix of the helically shaped portion 12 is not limited thereto, and may be clockwise along the longitudinal axis N of the shaft 10.

As shown in FIGS. 2A and 2B, the shaft 10 has a cross section that has an approximately rectangular shape extending in a direction perpendicular to the longitudinal axis N. Further, the cross section has a projection 14 that projects arcuately. In the present embodiment, the projection 14 is provided only on one side among four sides forming the approximately rectangular shape of the cross section. The other three sides of the cross sections form linear portions 15.

When the projection 14 is provided on one side among the sides forming a cross section, as compared to a configuration without any such projection 14 (a shaft having a rectangular shape in cross-section), the shaft 10 has a reduced contact area with a blood vessel wall, and thus applies a smaller force to the blood vessel wall when contacting the blood vessel wall.

Therefore, when rotating the shaft 10 and entering the inside of a blood vessel, contact resistance against a blood vessel wall is reduced. Accordingly, operation resistance of the shaft 10 as it is pushed and pulled is reduced so that torque transmission characteristics are enhanced, resulting in improved operability.

Moreover, even in a case where the above shaft 10 is inserted along an inverted U-shaped path from the lower extremity vasculature of the right leg into the lower extremity vasculature of the left leg by, for example, the Cross-Over method, when passing through the top of a blood vessel, sliding against the blood vessel wall and the like do not suppress movement of the shaft 10, so that a distal portion of the shaft 10 is allowed to be inserted deeply and smoothly into the blood vessel. In addition, it is possible to reduce damage of a blood vessel.

Here, it is possible to fabricate the shaft 10 of the present invention according to a method described below. First, a columnar metallic body is prepared to be rolled out from a predetermined direction. Thereafter, a rotary device is prepared, capable of applying rotary motion to a circumference of the metallic body having one end fixed, followed by rotation around a long axis of the metallic body from the other end.

Further, a distal end of the metallic body is fixed to one end of the rotary device while a proximal end of the metallic body is fixed to the other end of the rotary device, thereafter applying rotary motion from the other end of the rotary device, so that the metallic body is twisted from the proximal side. Thereby, the shaft 10 is formed, including the helically shaped portion 12 twisted evenly along a longitudinal direction.

The helically shaped portion 12 is twisted by the rotary device, and thereafter has stress applied by the twisting mitigated by means of heat treatment, thereby taking the form of a stable shape. A method of forming the helically shaped portion 12 is not limited to the above-described method, and may be fabricated by other known methods adopted appropriately.

FIG. 3 is a cross-sectional view showing an exemplary embodiment of the shaft of the present invention. Note that, in this figure, a cross section of the shaft is schematically illustrated, thus having a dimensional ratio different from the actual one.

In the shaft 10 shown in FIGS. 2A and 2B, the projection 14 is provided only on one side among sides forming a cross section, and linear portions 15 are provided on the other sides. In a shaft 20 shown in FIG. 3, projections 24 are formed on a pair of sides opposite each other. On sides except those having the pair of projections 24, linear portions 25 are provided, respectively.

As compared to a configuration without a projection (a shaft having a cross-sectional rectangular shape) and a configuration in which the projection 14 is provided only on one side among sides forming a cross section, the shaft 20 of the present embodiment has a reduced contact area with a blood vessel wall, and thus applies a smaller force to the blood vessel wall when contacting the blood vessel wall.

Therefore, when the above shaft 20 rotates and enters the inside of a blood vessel, contact resistance against a blood vessel wall is reduced. Accordingly, operation resistance of the shaft 20 as it is pushed and pulled is reduced so that sufficient torque transmission characteristics are secured, resulting in further improved operability.

FIG. 4 is a cross-sectional view showing an exemplary embodiment of the shaft of the present invention. Note that, in this figure, a cross section of the shaft is schematically illustrated, thus having a dimensional ratio different from the actual one.

In the shaft 20, the projections 24 are formed on a pair of sides opposite each other, and the linear portions 25 are respectively provided on sides except those having the pair of the projections 24. In a shaft 30, on sides except those with a pair of projections 34 among sides forming a cross section, recesses 37 recessed arcuately are provided, respectively. Here, the radius of curvature of the projection 34 is set so as to be approximately the same as the radius of curvature of a virtual circle S having a diameter equivalent to a long axis X of the cross section.

As compared to a configuration without a recess (such as a shaft having a cross-sectional rectangular shape), an area moment of inertia is lowered. Thus, for example, within a blood vessel of a lower extremity region extremely winding in an inverted U-shape, a permanent set (permanent deformation of the shaft) tends not to occur even in a case where the shaft 30 bends excessively due to a load applied thereto when coming into contact with a blood vessel wall, and the like. Accordingly, there is no possible trouble in subsequent operation, thereby making it easy to use the shaft 30 continuously.

FIG. 5 is a cross-sectional view showing an exemplary embodiment of the shaft of the present invention. Note that, in this figure, a cross section of the shaft is schematically illustrated, thus having a dimensional ratio different from the actual one.

In the above-described shaft 30, the radius of curvature of the pair of the projections 34 is set so as to be approximately the same as the radius of curvature of the virtual circle S having a diameter equivalent to the long axis X of the cross section. Whereas, in a cross section forming a shaft 40, the radius of curvature of a pair of projections 44 is smaller than the radius of curvature of the virtual circle S having a diameter equivalent to the long axis X of the cross section.

Such the shaft 40 has a cross section in a tapered shape, and has two tops of respective projections 44 in contact with a blood vessel wall. Therefore, comparing to not only a configuration without a projection (a configuration having a cross-sectional rectangular shape whose four corners are in contact with a blood vessel wall) but a configuration in which a projection is provided having the radius of curvature approximately the same as the radius of curvature of the virtual circle S, the shaft 40 reduces the contact areas (contact parts) with a blood vessel.

Accordingly, when the above shaft 40 rotates and enters the inside of a blood vessel, operation resistance of the shaft 40 as it is pushed and pulled is reduced so that sufficient torque transmission characteristics are secured, resulting in further enhanced operability. Furthermore, it is possible to reduce damage of a blood vessel.

FIG. 6 is a general view showing an exemplary embodiment of a guidewire of the present invention. In FIG. 6, a distal end of the guidewire to be inserted into the body is provided on the left, and a proximal end of the guidewire to be operated by a manipulator such as a doctor is provided on the right. Note that, in this figure, the guidewire is schematically illustrated, thus having a dimensional ratio different from the actual one.

A guidewire 100 shown in FIG. 6 is used for treatment of the lower extremity vasculature by, for example, the Cross-Over method. The guidewire 100 includes a core shaft 110, and a coiled body 120 covering a circumference of a distal portion of the core shaft 110.

First, a description will be given for the core shaft 110. The core shaft 110 includes a small diameter portion 110a, a tapered portion 110b and a large diameter portion 110c in order from the distal end to the proximal end. The small diameter portion 110a is a part on the most distal end of the core shaft 110 and is the most flexible part of the core shaft 110. The small diameter portion 110a is formed in a tabular shape by press working. The tapered portion 110b has a cross section formed in a tapered round shape whose diameter is gradually reduced toward the distal end. Note that, arrangements and dimensions of the small diameter portion 110a and the tapered portion 110b can be changed appropriately to obtain desired rigidity and the like. For example, the small diameter portion 110a may have a columnar shape. Further, the number of the tapered portions 110b and the angle of the tapered portion 110b may also be set appropriately as necessary.

The large diameter portion 110c is located on a proximal end of the coiled body 120, and takes on a shape similar to that of the shaft described above. That is, the proximal part of the core shaft 110 that is exposed from the coiled body 120 is twisted along a longitudinal direction, and has a helically shaped portion 112. Moreover, as described above, a cross section of the helically shaped portion 112 may have a pair of the projections 34 projected arcuately.

Thereby, comparing to a configuration without any projection 34 (a shaft having a cross-sectional rectangular shape), the guidewire 100 of the present embodiment has reduced contact areas (contact parts) with a blood vessel wall. Accordingly, when the guidewire 100 rotates and enters the inside of a blood vessel, operation resistance of the guidewire 100 as it is pushed and pulled is reduced so that sufficient torque transmission characteristics are secured, resulting in further enhanced operability. Furthermore, it is possible to reduce damage of a blood vessel.

Note that in the above description, the guidewire 100 includes the large diameter portion 110c having the same shape as that of the shaft shown in FIG. 4 including the projections 34. However, the shape of the large diameter portion 110c is not limited thereto. The large diameter portion may have the same shape as any of those described above. With any of the above shapes of the shaft as the large diameter portion, operation resistance of the guidewire 100 as it is pushed and pulled is reduced so that sufficient torque transmission characteristics are secured, resulting in further enhanced operability.

The core shaft 110 can be formed using materials such as, but not limited to, stainless steel (SUS304), a super elastic alloy such as a Ni—Ti alloy, and a piano wire.

Next, description will be given for the coiled body 120. The coiled body 120 in the present embodiment is a single thread coil composed of wires wound helically.

As shown in FIG. 6, a distal end of the coiled body 120 is fixed to a distal end of the core shaft 110 with a distal end joint 151. A proximal end of the coiled body 120 is fixed to the core shaft 110 with a proximal end joint 153. Further, an approximately middle part of the coiled body 120 located distally from the proximal end joint 153 and proximally from the distal end joint 151 is fixed to the core shaft 110 with a middle joint 155.

Materials forming the distal end joint 151, the proximal end joint 153 and the middle joint 155 are not especially limited, but include, for example, brazing metal such as a Sn—Pb alloy, a Pb—Ag alloy, a Sn—Ag alloy and a Au—Su alloy.

Materials forming the coiled body 120 are not especially limited, but can employ a radiopaque wire or a radiolucent wire. Materials used for a radiopaque wire are not especially limited, but can include, for example, gold, platinum, tungsten, an alloy containing these elements (for example, a platinum-nickel alloy), or the like. Moreover, materials used for a radiolucent wire are not especially limited, but can include, for example, stainless steel (SUS304, SUS316 and the like), a super elastic alloy such as an Ni—Ti alloy, a piano wire and the like.

FIG. 7 is a general view showing an exemplary embodiment of a guidewire of the present invention. In FIG. 7, a distal end of the guidewire to be inserted into the body is provided on the left, and a proximal end of the guidewire to be operated by a manipulator such as a doctor is provided on the right. Note that, in this figure, the guidewire is schematically illustrated, thus having a dimensional ratio different from the actual one.

A guidewire 200 of the present embodiment has a configuration of a coiled body different from that shown in FIG. 6. That is, a coiled body 320 employed in the guidewire 200 is composed of a plurality of helically wound strands 322 (eight strands in the present embodiment), the strand 322 being made of a core wire (wire) 322a and six side lines (wires) 322b wound so as to cover a circumference of the core wire 322a. Materials forming the core wire 322a and the side line 322b are not especially limited, but include, for example, stainless steel, tungsten, a Ni—Ti alloy and the like.

According to the guidewire 200 of the present embodiment, comparing to a guidewire including a coiled body composed of, for example, a single wire having an external diameter nearly equal to that of the guidewire 200, flexibility of the coiled body is improved, thereby making it possible to secure sufficient torque transmission characteristics. Further, breaking strength against twisting is improved, so that safety of the guidewire 200 is enhanced.

What is claimed is:

1. A shaft comprising:
a twisted elongated body that twists along a longitudinal axis of the elongated body,
wherein a cross section of the elongated body includes a rectangular shape and a first arcuate projection, the rectangular shape being elongated in a first direction perpendicular to the longitudinal axis.

2. The shaft according to claim 1, wherein the cross section of the elongated body includes a second arcuate projection, the first arcuate projection and the second arcuate projection being disposed on a first pair of opposite sides of the cross section.

3. The shaft according to claim 2, wherein the cross section of the elongated body includes a first arcuate recess and a second arcuate recess disposed on a second pair of opposite sides of the cross section.

4. The shaft according to claim 3, wherein a radius of curvature of the first and second arcuate projections is smaller than a radius of curvature of a virtual circle having a diameter equivalent to a length of the cross section in the first direction.

5. The shaft according to claim 3, wherein a radius of curvature of the first and second arcuate projections is equal to a radius of curvature of a virtual circle having a diameter equivalent to a length of the cross section in the first direction.

6. A guidewire comprising:
a core shaft; and
a coiled body covering a distal portion of the core shaft, wherein:
the core shaft includes a proximal portion disposed proximally of the coiled body,
the proximal portion of the core shaft includes a twisted elongated body that twists along a longitudinal axis of the proximal portion,
a cross section of the elongated body includes a rectangular shape and a first arcuate projection, the rectangular shape extending in a first direction perpendicular to the longitudinal axis.

7. The guidewire according to claim 6, wherein the cross section of the elongated body includes a second arcuate projection, the first arcuate projection and the second arcuate projection being disposed on a first pair of opposite sides of the cross section.

8. The guidewire according to claim 7, wherein the cross section of the elongated body includes a first arcuate recess and a second arcuate recess disposed on a second pair of opposite sides of the cross section.

9. The guidewire according claim 8, wherein a radius of curvature of the first and second arcuate projections is smaller than a radius of curvature of a virtual circle having a diameter equivalent to a length of the cross section in the first direction.

10. The shaft according to claim 8, wherein a radius of curvature of the first and second arcuate projections is equal to a radius of curvature of a virtual circle having a diameter equivalent to a length of the cross section in the first direction.

11. The guidewire according to claim 6, wherein the coiled body comprises a plurality of helically wound strands, each of the strands including a plurality of twined wires.

* * * * *